United States Patent [19]

LeVeen et al.

[11] Patent Number: 4,695,956

[45] Date of Patent: Sep. 22, 1987

[54] APPARATUS AND METHOD OF QUANTIFYING HEMOSTASIS USING OSCILLATIONS FROM A TRANSDUCER IMMERSED IN THE BLOOD SAMPLE

[76] Inventors: Eric G. LeVeen, 321 Confederate Cir., Charleston, S.C. 29407; Robert F. LeVeen, 312 Lombard St., Philadelphia, Pa. 19147

[21] Appl. No.: 667,007

[22] Filed: Nov. 1, 1984

[51] Int. Cl.⁴ ............................................. G06F 15/42
[52] U.S. Cl. .......................................... 364/416; 73/54
[58] Field of Search ................... 364/413, 416; 73/54, 73/64.1, 55; 128/638, 637

[56] References Cited

U.S. PATENT DOCUMENTS

| | | | |
|---|---|---|---|
| 3,587,295 | 6/1971 | Simons | 73/64.1 |
| 3,878,374 | 4/1975 | Schlatter | 364/718 |
| 3,903,731 | 9/1975 | Sieben | 73/54 |
| 3,903,732 | 9/1975 | Rork | 73/54 |
| 3,943,753 | 3/1976 | Simon | 73/54 |
| 4,023,400 | 5/1977 | November | 73/54 |
| 4,292,673 | 9/1981 | DuBae | 73/54 |
| 4,341,111 | 7/1982 | Husar | 73/59 |

Primary Examiner—Jerry Smith
Assistant Examiner—Gail Hayes
Attorney, Agent, or Firm—John S. Hale

[57] ABSTRACT

An apparatus and method of use thereof which quantifies the processes of hemostasis occuring in human blood. The apparatus utilizes an oscillator transducer which is sensitive to changes of viscosity and tensile strength of surrounding blood as coagulation occurs in the latter. An oscillator, which may be excited to oscillate at a natural resonant frequency, is housed within an enclosure designed to accommodate a finite quantity of blood in contact with the oscillator. As hemostasis occurs, the frequency at which the oscillator resonates is impaired. A control and computation system for measurement of the change of frequency is coupled to the oscillator, which counts the number of oscillations of the oscillator transducer during a predetermined time period, and computes the frequency as a function of the known time period and the counted oscillations.

9 Claims, 7 Drawing Figures

APPARATUS AND METHOD OF QUANTIFYING HEMOSTASIS USING OSCILLATIONS FROM A TRANSDUCER IMMERSED IN THE BLOOD SAMPLE

RELATED APPLICATIONS

This application is related to U.S. patent application Ser. No. 521,840 filed Aug. 10, 1983.

BACKGROUND OF THE INVENTION

The present invention relates to the medical arts, and in particular, sets forth a method and apparatus for the measurement of numerous blood parameters relating to hemostasis.

Hemostasis is that process which arrests the flow of blood from damaged blood vessels. The ability to stop bleeding is fundamentally important not only in the obvious cases of trauma and surgery but is also essential on a day to day basis for arresting bleeding from hundreds of microvascular injuries that occur from normal activity. The manifestations of prolonged uncontrolled bleeding include impaired oxygen carrying capacity, which may fall below life sustaining levels, and formation of blood accumulations called "Hematomas" which can cause mass necrosis in their immediate vicinity. For these and other reasons, the measurement of the various parameters of hemostasis are extremely important laboratory tests which allow patients with abnormal bleeding to be identified thereby indicating preventive measures to be undertaken.

In order to understand the various measurements made by the present invention, the processes that define hemostasis must be examined. The mechanisms employed by the body to alleviate blood flow from injured blood vessels involves the interrelations of three separate functions: the vascular system, platelet function, and the process of blood coagulation. The ultimate goal of these mechanisms is to stem blood loss over the immediate, intermediate and long term periods, respectively, and cumulatively define hemostasis.

Vascular Phase

Injury to blood vessels is the initial event that activates the processes of hemostasis. The first physiological response to reduce blood loss involves the injured vessel itself. Blood loss through the injured vessel is decreased by vasoconstriction proximal to the site of the damage. Vasoconstrictions, as the name implies, involve constriction or narrowing of the injured blood vessels thereby reducing bulk blood flow. This vasoconstriction not only serves to decrease blood loss but also results in a relative stagnation of blood flow around the damaged area allowing local accumulations of active elements for coagulation to arise, preventing the washout/dilution effect of normal blood flow.

Another function of damaged blood vessels is the activation of the second "platelet" and third "coagulation" phases of hemostasis. The activations are passive processes that simply involve the exposure of blood components to subendothelial blood vessel components. The inside of normal blood vessels are lined by endothelial cells; it is these cells that are constantly exposed to blood flowing through the vessels. Endothelial cells that plate the inside of blood vessels comprise the endothelial surface. This surface is very smooth and slick and secretes minute quantities of a substance which actually inhibits the platelet and coagulation phases of hemostasis thereby serving to protect against activations of the clotting mechanisms in the intact blood vessel. However, just below the endothelium lies the subendothelium which is normally not in contact with the blood. It is the exposure of these subendothelial components such as collagen which activates the second and third phases of hemostasis when vessels are injured.

Platelet Phase

Platelets are small anucleated cells that exist in the blood stream in concentrations of 150,000 to 450,000 cells per milliliter; they function almost exclusively in the process of hemostasis. These cells normally circulate as inactive components of blood, and activate on their exposure to subendothelial components as described above, as well as by certain biochemical mediators, namely, prostaglandins and thromboxanes. These changes that occur in platelets and the subsequent properties and manifestations can be described by six steps occuring sequentially.

Step 1: Adhesion—Adhesion involves the attachment of platelets to the activating substances described above.

Step 2 through 5: Platelet Release Reactions—The platelet release reactions involve the active extrusion of biologically active substances from the platelets. The mechanism of extrusion involves the "squeezing" of the platelet. This contraction of the platelet also alters its shape from the smooth, discloid shape it originally travels in, to a spiny, sphere shape which is more adept at interlocking in the primary hemostatic plug as described above. Many substances are released from the platelets and they assist in virtually every phase of healing and defense; of special note however, is the release of further ADP which further precipitates steps 2 through 5 in an "Autocascade" phenomenon that accelerates the steps needed for formation of the primary hemostatic plug and arresting of further blood loss. Also released at this time are prostaglandins and thromboxanes which, as previously described, are potent platelet activators.

Step 6: Clot Retraction—Step 6 occurs long after the first five steps above which involve the formation of the primary hemostatic plug. Clot retraction involves the interaction of both platelets and fibrin, a product which is the end result of coagulation. Platelets attach to points of intersection along various fibrin strands by means of cellular extension or cellular "arms". These "arms" then contract and thereby shrink the fibrin mesh to approximately 70% to 80% of its original volume. This process is well described in the physiological literature.

Coagulation Phase

Coagulation is the process involved in the formation of fibrin; fibrin is the backbone or skeletal portion of the permanent hemostatic plug. The formation of fibrin involves a complex interaction of pathways and enzymes.

Fibrin is an insoluable, rod-shaped protein with a very high potential strength. As it is formed by the processes described above, it is deposited at the site of injury where it interacts with platelets to close the wound permanently and allow complete healing, repair and restoration of normal function.

Given the complexity of the Hemostatic processes, the problem of devising a singular laboratory test to check on the various parameters of the process is formidable. Current therapy methods may indicate any number of the following tests: (1) whole blood clotting time—this is the time needed for one milliliter of blood to clot at 37 degrees celsius in a glass test tube as measured by a stop watch. This test provides only a rather gross approximation of the overall strength of the hemostatic process. (2) Partial Thromboplastin Time ("PTT")—This is the time required for recalcified, citrated plasma to clot in presence of tissue thromboplastin; this is an active measure of one of the key mechanisms of hemostasis. (3) Thrombin Clotting Time—the time required for citrated plasma to clot in the presence of added thrombin. (4) Bleeding Time—the time required for a one centimeter long, one milimeter deep laceration to stop bleeding. (5) The Platelet Time ("PT")—the measure of increases in light transmitted through a test tube containing high concentrations of platelets in plasma with added platelet activating agents added to the solution. As the platelets aggregate, more light is transmitted through this solution. (6) The Thromboelastograph—this test checks the tensile strength of the fibrin clot.

Calcium is present in blood in nominal concentrations and is responsible for activation of the various steps in coagulation. By adding a binding agent, for instance citrate, to the blood as it is drawn from the patient, the binding agent combines with the calcium thereby preventing any of the steps from occuring until such time as the sample can be directed to the lab at which time more calcium is added and the processes can be allowed to occur under the supervision of an appropriate lab technician with parameters quantified. During antiplatelet and anticoagulation therapy for angina pectoralis and stroke victims, the PT, PTT and platelet tests can verify that treatment is therapeutic. In other words, it is verified that medication sufficiently elevates the desired parameters without reaching toxic levels which could induce spontaneous bleeding.

All these tests are used very frequently in hospital and patient care settings for the screening of numerous types of conditions. Several examples are listed below:

Bleeding disorders can be detected. All of the above tests are indications of the various properties of anti-bleeding mechanisms that the body employs. A series of such tests can determine if a given patient has an abnormal bleeding time and therefore might be at especially high risk for surgical intervention. These patients can be identified and deficient factors can be identified and replaced.

Abnormal hemostasis is often present in an otherwise normal patient when the patient is affected by disease which alters the hemostatic properties. For instance, liver disease can result in the impairment of the synthesis of various coagulation factors which are normally synthesized in the liver thereby manifesting itself as a bleeding disorder.

Certain chemicals and poisons can lead to hemostatic abnormalities.

In certain patients the hemostatic properties might be activated at times when they should not. This can lead to formation of clots in otherwise intact vessels, obstructing blood flow and causing blood deficiency in certain tissues. These clots can also break off with the emboli travelling to distant parts of the arterial system and blocking the system when wedged into the smaller distal arteries.

The PT and PTT are also an indication of liver function as all the factors responsible for these pathways are synthesised in the liver. Liver function may therefore be assessed indirectly by measuring the blood's PT and PTT's.

Although these tests are used daily and figure prominently in the care of hospitalized patients, all the techniques required for the above tests are very time consuming, costly, and are not readily available without a completely equipped chemistry laboratory.

The Thromboelastograph has the advantage in that it describes an easily understood parameter, namely, that of the tensile strength of the clot, and can measure the reaction time required for clot formation to begin. The reaction time is followed by a variable interval which is required for the clot to develop its maximal strength. It also measures whether there are any forces causing clotlysis or clot destruction. Clotlysis can intervene after a clot has formed and reinstitute bleeding from the previously closed wound.

In addition to the advantage of diagnosing coagulation deficiencies the Thromboelastograph generates an image which is understandable by physicians not intimately involved with hemotology and the coagulation process; therefore interpretation is simplified. The Thromboelastogram has the further advantage that it displays all the clotting parameters and allows for a diagnosis of deficiency for any one of the previously described coagulation factors whereas the more commonly used tests contemplate only one aspect of the clotting parameter at a time. Nonetheless the Thromboelastogram has several serious drawbacks. The primary deficiency is the expense of such a device. Further, it requires specially trained laboratory technicians for proper usage and it consumes a great deal of time. Because the apparatus used to generate the Thromboelastogram is expensive, rarely is more than one such instrument present in any given hospital. Further, it can only analyze one sample at a time and therefore cannot be used for mass screening which is essential for efficient hospital use. The apparatus itself is fragile since it involves a torsion wire with motor driven cup which must be specially cleaned and properly paced if the test is to be a valid indicator of a coagulation defect.

It is the above noted drawbacks that the present invention addresses itself to, and not only circumvents these, but expands upon the scope of the Thromboelastograph vis-a-vis the mutifarious stages of hemostasis as set forth above.

SUMMARY OF THE INVENTION

The present invention has all the advantages of the Thromboelastograph and numerous advantages superior to those present in the Thromboelastograph. Like the Thromboelastograph, the visual diagram can be generated, and the information can be digitized facilitating computerized interpretation. The apparatus has no moving parts and makes possible the mass screening of coagulation defects as well as the monitoring of hepprin therapy and clot dissolution as earlier described. The inventive device can be used by unskilled personnel. Further, more than one determination can be made by utilizing multiple sensors. The apparatus has greater uniformity than the Fibroelastogram since it utilizes well known electronic measurements and can be standardized as results are reproducible.

The present invention utilizes an oscillating crystal which is capable of oscillating in the lower kilohertz range, namely, from 100 hertz to 1 megahertz. A long slender crystal is placed adjacent to and spaced apart from a solid structure, with vibrations of the crystal causing the distance between them to alternately enlarge and contract. This change occurs at a definite frequency when plasma is placed in the void between the crystal and the stationary post owing to a specific resonant frequency. The plasma is subjected to elongation and compression by the oscillating crystal. The change in physical state from the fluid phase of blood to the gel phase of blood, which is the clotted blood phase, decreases the frequency of oscillations in proportion to the strength of the blood clot formed between the oscilating crystal and the stable base. The strength of this clot is dependent on the fibrin content of the blood and the strength of the fibrin molecule. As the fibrin molecule is cleaved by fibrinolysis, the strength of the fibrin clot will decrease and the frequency of the oscillations will proportionally increase. The time interval required for the transformation of plasma from liquid phase to gel phase is equivalent to the reaction time on the Thromboelastogram. The oscillating frequency is measured by standard circuitry as fully set forth below. The frequency of oscillation is recorded against time and the information can be generated in graphic form or as a digital readout.

The void between the vibrating crystal and the solid post is constructed to maintain a known volume of blood which is held in the interval void. A void of small cross-section can be filled by capillary action. Capillary action, or "capillarity" is an inherent property of aqueous solutions, including blood. In such the same way as water can be soaked up into a paper towel, blood can be "soaked in" to a very small space between the oscillating crystal and the solid post. Thus the calliparity phenomenon can be advantageously used to load blood into the present invention. Applicant believes this to be the best mode and preferred embodiment of the present invention.

Alternatively, the crystal and post can be immersed directly into a small liquid pool of plasma with the speed of oscillation measured before, during and after clot formation. Still another variation in method is to coat the sides of the crystal with a conducting substance so that the change in amplitude of the vibrations can be measured by a change in capacitance of the metallic pieces on the two sides of the vibrating crystal. In other words, the amplitude of the oscillation can be measured by this and by other methods for the oscillation will change as a liquid phase changes to gel phase since the forces required to elongate and compress the gel become greater, causing the amplitude to diminish. The changes in amplitude can be measured in addition to the changes in frequency. This change can also be displayed visually against time.

These and other aspects and advantages of the present invention will become more readily apparent by reference to the following detailed description thereof when read in combination with the accompanying drawings.

DETAILED DESCRIPTION OF THE DRAWINGS

Figure 7:
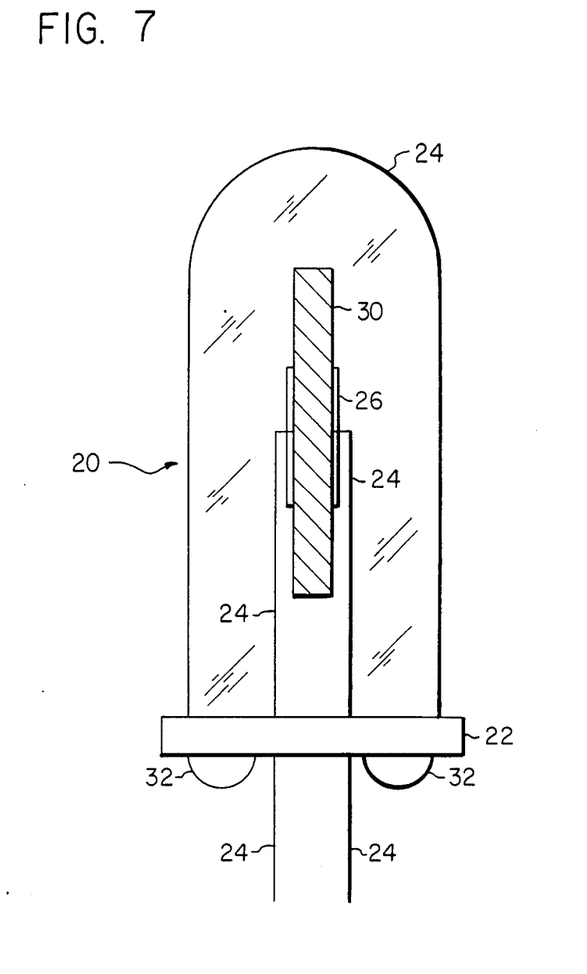
FIG. 7 is an isolated side view of an oscillator transducer according to the present invention.

The best mode and preferred embodiment of the present invention is disclosed in FIGS. 1 through 7. Turning first to FIG. 7, a transducer structure 20 in accordance with the invention comprises a base 22, a pair of electrodes 24 extending through the base 22, an oscillator 30, and contact plates 26 mounted to oscillator 30, each being connected to a respective electrode 24. While oscillator 30 is preferably a quartz crystal, it may also be any well-known conventional oscillator which does not react with any of the components of blood to which it is exposed. The electrodes 24 and plates 26 on opposite sides of oscillator 30 may serve to suspend oscillator 30 above base 22, or any other conventional manner of mounting oscillator 30 may be utilized. Container 34 may be of any substance which is not permeable to blood. Input channels 32 define apertures through which the blood fills container 34. Blood may be actively induced through input channels 32 by standard aqueous pumps or gravity if transducer structure 20 is inverted. In the preferred embodiment, the integral defined by container 34 and oscillator 30 is of slight width, less than 1 millimeter, blood may be introduced to input channels 32 and container 34 is passively filled by capillary action.

Figure 1:
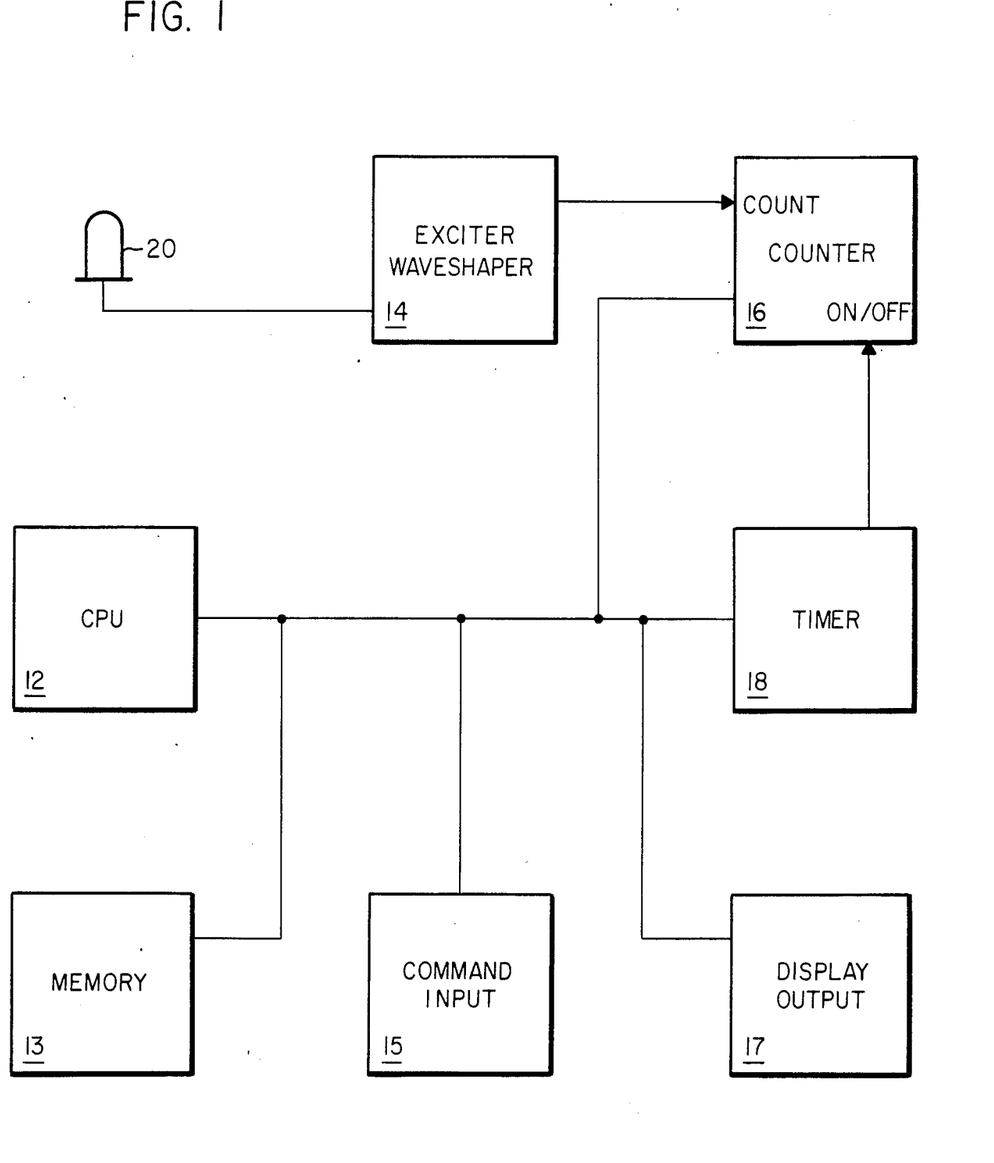
FIG. 1 is a block diagram of an oscillator transducer and control and computation system according to the present invention.

Turning now to FIG. 1, the oscillator transducer 20 may be coupled by electrodes 24 to an exciter and wave-shaper 14 which provides energy for the oscillator 30 and shapes the sinusoidal piezoelectric output wave form to conform to the voltage and current requirements for digital circuitry. The output of exciter and wave-shaper 14 is coupled to the count input of counter 16. Counter 16 is also coupled to timer 18 which, upon activation, enables the count input of counter 16, waits a predetermined time period, and then disables the count input of counter 16. Central processing unit (CPU) 12 is coupled to timer 18 and may be utilized to alter the predetermined time as well as initiate the timing sequence. CPU 12 is also coupled to counter 16 and may be utilized to initialize a value in counter 16 which is subsequently incremented or decremented by the output of exciter and wave-shaper 14, as well as to retrieve the final status of counter 16 after timer 18 has disabled the count input. CPU 12 is further coupled to memory 13, command input 15 and display output 17. Memory 13 serves as both temporary data storage and permanent program storage, while command input 15 allows a user to select program options and display output 17 allows presentation of computation results in human-readable form.

FIGS. 2 through 6 disclose an automated control and computation system corresponding to the system of FIG. 1. It should be noted that the nomenclature for these drawings includes the following prefixes: IC for integrated circuit, R for a resistor, Q for a transistor, C for a capacitor, G for a gate, U for a crystal, A for a line comprising a portion of a group of parallel lines within an Address bus, and D for a line comprising a portion of a group of lines within a Data bus. Labels placed within a block indicator of an integrated circuit refer to pin function designators for that circuit according to the standard data sheet descriptions of such integrated circuits available from their manufacturers.

Figure 2:
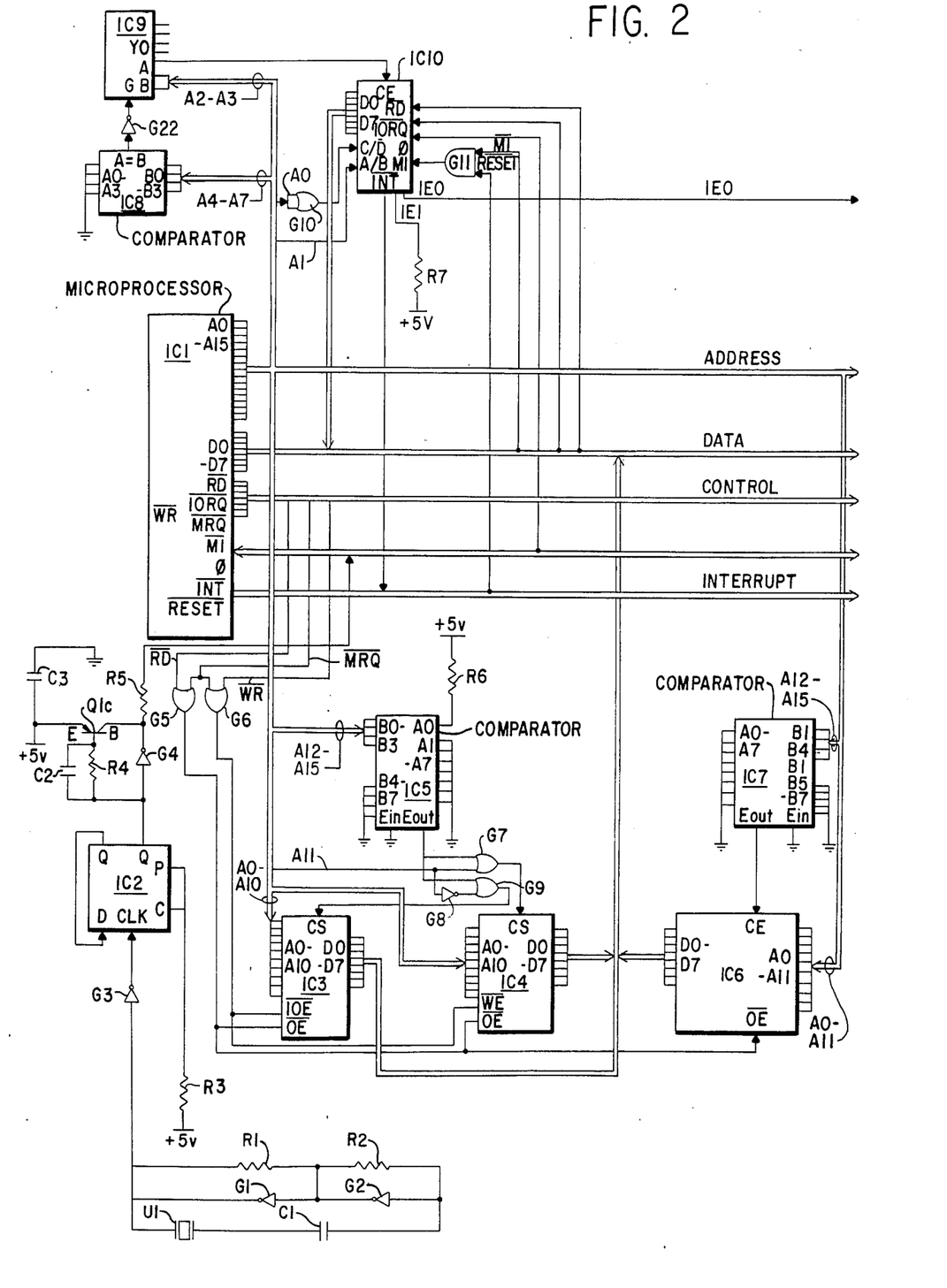
FIG. 2 is a circuit diagram of a portion of the control and computation system of FIG. 1, illustrating a central processing unit, memory and other devices.

Turning now to FIG. 2, a processor IC1 is provided. In this particular embodiment, IC1 is preferably a Z80 microprocessor, such as is available off-the-shelf from Zilog. Of course, it is recognized that other microprocessors may be utilized without departing from the overall design or philosophy of the system, although different microprocessors may require different associated integrated circuits for control of input/output and memory functions. The microprocessor IC1 controls the 16-line address bus comprising individual lines A0 through A15; A0 is the least significant bit of the bus. The microprocessor is also coupled to the 8-line data bus comprising data lines D0 through D7; D0 is the least significant bit of the bus. Additionally, four control outputs are provided and designated RD, IORQ, MRQ and M1, all of which are active-low. Processor inputs include a master clock input from an external oscillating circuit, and interrupt inputs NMI, INT and RESET. The interrupt inputs are also active-low.

A crystal excitation and wave-shaping circuit is utilized to produce a master clock signal. Crystal U1 is coupled in series with capacitor C1. C1 is also coupled to the input of inverters G2, and the output of G2 is coupled to the input of inverter G1. Resistor R2 is coupled across the input and output of G2, and resistor R1 is coupled across the input and output of G1. The output of G1 is also coupled to U1 and C1, as well as through inverter G3 to the clock input of IC2, a type D flipflop. The preset and clear inputs of IC2 are coupled through pull-up resistor R3 to a five volt source, and the inverted Q output is coupled to the D input. The Q output is coupled through inverter G4 and resistor R5 to the clock line. The output Q of IC2 is also coupled through resistor R4 and capacitor C2 in parallel to the base of transistor Q1. The collector of Q1 is coupled to the output of G4. The emitter of Q1 is coupled to a five volt source and through capacitor C3 to ground.

OR gates G5 and G6 are utilized to enable the input and output to various memory circuits. The inputs of G5 are the read line and the MRQ memory request line, and the inputs of G6 are the write line WR and the MRQ memory request line. In the Z80, MR0 is utilized to distinguish between a valid memory address on the address bus and a valid input-output device address on the address bus. In the latter instance, the IORQ input/output request line is activated. The output of G5 is coupled to the output enable OE inputs of IC3, IC4 and IC6. The output of G6 is coupled to the input enable WE inputs of IC3 and IC4. IC3 and IC4 are preferably 2K by 8-bit random access memory circuits, and IC6 is preferably 4K by 8-bit read only memory.

The outputs D0 through D7 of IC6 are coupled to the corresponding lines of the data bus, and the address inputs A0 through A11 are coupled to the corresponding lines of the address bus. IC7 serves to decode and upper four lines of the address bus A12 through A15, and the output E-OUT of IC7 is coupled to the chip enable CE input of IC6. IC7 is an 8-bit comparator with inputs A0 through A7 grounded, inputs B0 and B5 through B7 grounded, and inputs B1 through B4 coupled to address bus lines A12 through A15, respectively. Thus, in this particular embodiment, IC6 is decoded to the first 4K block of memory within the system.

IC5 is an 8-bit comparator similar to IC7, with inputs B0 through B3 coupled to lines A12 through A15 of the address bus respectively. Inputs B4 through B7 are grounded, as are inputs A1 through A7 and E-IN. Input A0 is tied through pull-up resistor R6 to a five volt source. Thus, the output pin E-OUT of IC5 will indicate an equivalence when address line A12 is at a high value, while lines A13 through A15 are at a low value.

E-OUT of IC5 is coupled to an input of each of OR gates G7 and G9. Address line A11 is coupled to a second output of G7, and through inverter G8 to a second input of G9. The output of G7 is coupled to the CS chip select input of IC4 and the output of G9 is coupled to the CS chip select input of IC3. The pins D0 through D7 of IC3 and IC4 are coupled to the corresponding data lines of the data bus. The inputs A0 through A10 of IC3 and IC4 are coupled to the corresponding lines of the address bus. Thus, IC4 is decoded to provide a 2K random access memory block beginning at location 4096 decimal, and IC3 is decoded to provide a 2K random access memory block beginning at location 6144 decimal. IC10 is a Z80 PIO support circuit which is utilized to handle keyboard input and display output in the preferred embodiment. Pins D0 through D7 of IC10 are coupled to the corresponding lines of the data bus. The preferred embodiment utilizes the standard daisy-chain interrupt priority structure, and IC10 is at the top of the chain. Therefore, the interrupt INT output of IC10 is coupled to the INT input of IC1, and the input IEI of IC10 is coupled through pull-up register R7 to a five volt source. Other inputs to IC10 include the master clock signal from R5, the RD and IORQ lines from the control bus, the port A/B selector which is coupled to line A1 of the address bus, and the command/data C/D input selector to which is coupled to address bus line A0 through both inputs of NOR gate G10. Additionally, the reset interrupt line and the M1 control line are coupled to the inputs of AND gate G11 and the output of G11 is coupled to the M1 input of IC10. Because IC10 is treated as an I/O device rather than a memory device, only the least significant 8 lines of the address bus, A0 through A7, need be decoded. Lines A4 through A7 are coupled to inputs B0 through B3 respectively of IC8, which is a 4-bit comparator. The four IC8 inputs A0 through A3 are coupled to ground, and the output A=B is coupled through inverter G22 to the G input of IC9, which is a 2-to-4 decoder. Address lines A2 and A3 are coupled to the A and B inputs, respectively, of IC9, and the Y0 output of IC9 is coupled to the chip enable input of IC10. Thus, IC10 will be enabled only when address lines A2 through A7 are grounded, while the least significant address bit A0 will select whether a command or data is to be handled, and address bit A1 will select whether ports A or B of IC10 will be affected. These ports and the input/output devices coupled thereto are illustrated more fully in FIG. 6, described below.

Figures 4, 6:
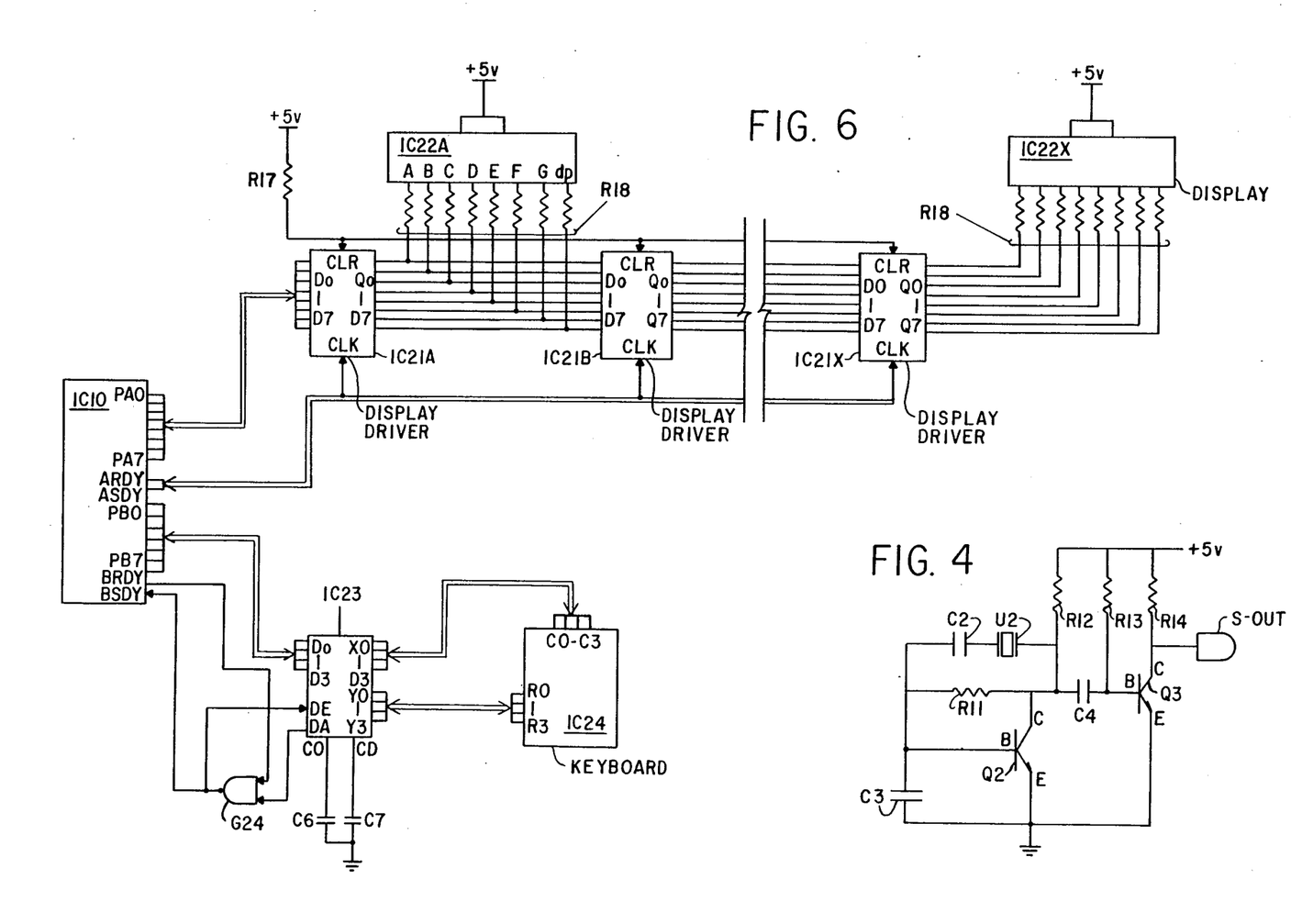
FIG. 4 is a circuit diagram of a portion of the control and computation system of FIG. 1, showing an oscillator transducer exciter and wave-shaper.
FIG. 6 is a circuit diagram of a portion of the conrol and computation system of FIG. 1, showing keyboard input and display output.

Turning now to FIG. 4, an excitation circuit for test crystal U2 is illustrated. One terminal of U2 is coupled to the collector transistor Q2, and the other terminal of U2 is coupled through capacitor C2 to the base of Q2.

Capacitor C3 couples the base of Q2 to ground, and the emitter of Q2 is also grounded. A five volt source is coupled through resistor R12 to the collector of Q2 and through resistor R13 to the base of transistor Q3. The collector of Q2 is also coupled through capacitor C4 to the base of Q3. The collector of Q3 is coupled through resistor R14 to a five volt source, and the emitter of Q3 is grounded. The collector of Q3 forms signal output point S-OUT.

Figure 3:
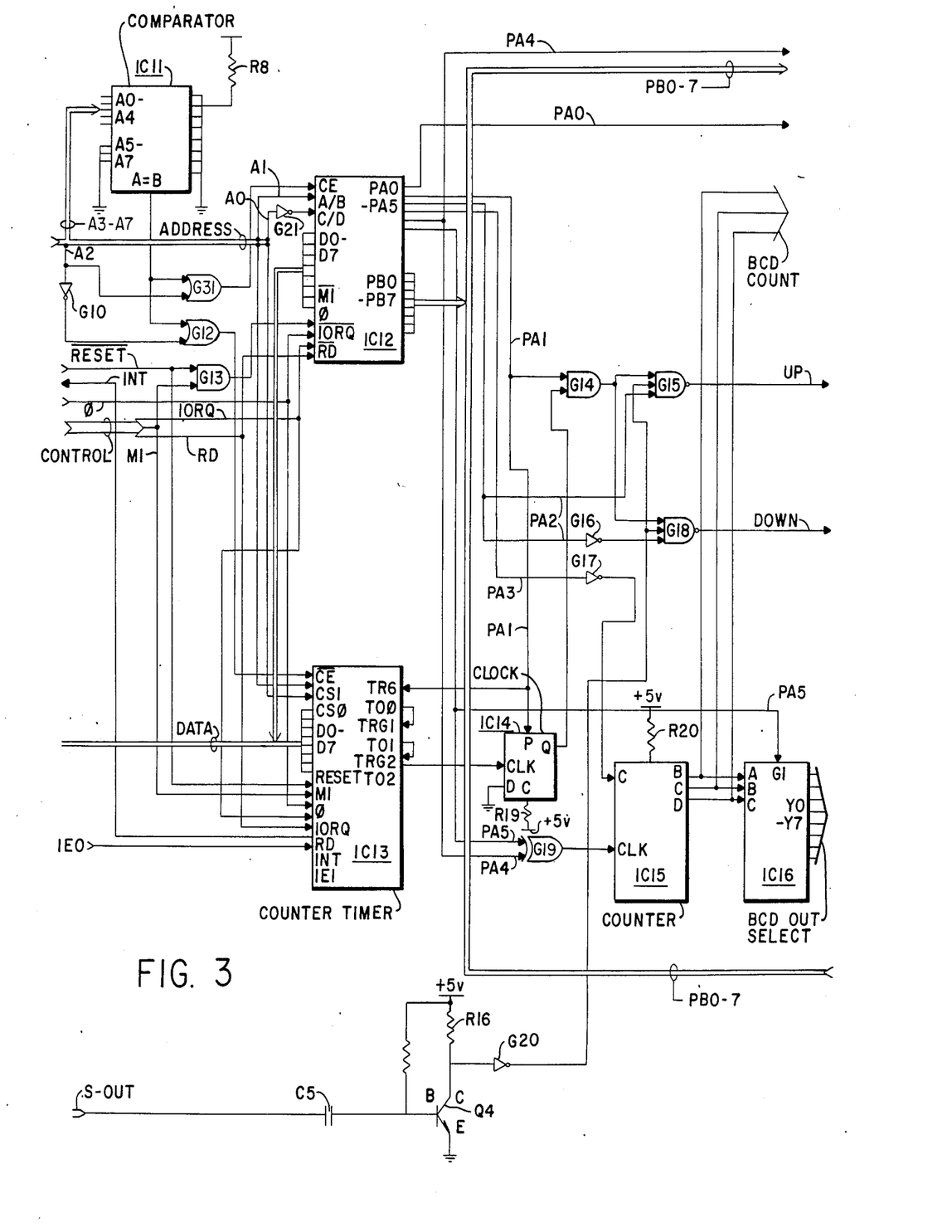
FIG. 3 is a circuit diagram of another portion of the control and computation system of FIG. 1, showing counter controls and other devices.

Turning now to FIG. 3, S-OUT is coupled through capacitor C5 to the base of transistor Q4. A five volt source is also coupled through resistor R15 to the base of Q4. The emitter of Q4 is grounded, and the collector of Q4 is coupled through resistor R16 to a five volt source. The collector of Q4 is also coupled to the input of inverter G20, the output of which is a square wave with TTL voltage and current level, corresponding in frequency to that of the signal emitted by U2.

IC12 is a second PIO, and IC13 is a Z80 CTC counter-timer, which together control the functions which convert the output of G20 to a digital numeric representation for further processing and analysis. Address decoding for both IC12 and IC13 is provided by 8-bit comparator IC11. Inputs A5 through A7 of IC11 are grounded, and inputs A0 through A4 are coupled to address lines A3 through A7, respectively. No higher address lines need be decoded since IC12 and IC13 are also treated as I/O devices. Inputs B0 and B2 through B7 of IC11 are grounded, and input B1 is coupled through pull-up register R8 to a five volt source. The equivalence output of IC11 is coupled to an input of each of OR gates G31 and G12. Address line A2 is coupled to a second input of G11, and through inverter G10 to a second input of G12. The output of G11 is coupled to the chip enable CE input of IC12, and the output of G12 is coupled to the chip enable CE input of IC13. Address line A1 is coupled to the port A/B select input of IC12, and address lines A0 is coupled through converter G21 to the control/data select input of IC12. Thus, IC12 occupies I/O locations 16, 17, 18 and 19. Address line A0 is also coupled to the channel select zero CS0 input of IC13, and address line A1 is coupled to the channel select one CS1 input of IC13. Thus, IC13 occupies I/O locations 20, 21, 22 and 23.

Both IC12 and IC13 have their inputs for master clock, IORQ and RD coupled to the corresponding bus lines. Also, their data pins D0 through D7 are coupled to the corresponding lines of the data bus. The reset input of IC 13 is coupled directly to the M1 line. These lines are coupled to the inputs of AND gate G13, and the output of G13 is coupled to the M1 input of IC12. As the next stage in the interrupt daisy-chain, the input IEI of IC13 is coupled to the output IEO of IC10. Thus, IC13 can issue an interrupt request only when IC10 has not done so.

In this embodiment, port B of IC12 is utilized to initialize and collect data, while port A is utilized to control the sequence of data collection events. IC13 is utilized as a timer to allow the counting of pulses from G20 during a predetermined interval, and then stop that counting. To this end, three of the four timers of IC13 have been chained together. The trigger input of timer 0 is coupled to pin 1 of IC12 port A (the pins of which will hereinafter be designated as PAx). The overflow output of IC13 timer 0 is chained to the trigger input of IC13 timer 1. The overflow output of timer 1 is chained to the trigger input of IC13 timer 2, and the overflow output of timer 2 is coupled to the clock input of IC14, a standard D-type flip-flop. PA1 is coupled directly to the preset input of IC14, the D input of IC14 is grounded, and the clear input of IC14 is coupled through pull-up resistor R19. The Q output of IC14 is coupled to one input of AND gate G14 and the second input of G14 is coupled to PA1. The output of G14 is coupled to one input of each of 3-input NAND gates G15 and G18. A second input of each of G15 and G18 is coupled to the output of G20. The third input of G15 is coupled to PA2, and PA2 is coupled through inverter G16 to the third input of G18. As will be more fully explained below, the output of G15 increments a counter and is labelled UP, while the output of G18 decrements the counter and is labelled DOWN. In this embodiment, either UP or DOWN may transfer G20 signals to the counter stages, but not both simultaneously. The status of PA2 selects which of G15 and G18 will be active, while both may be deactivated if PA1 is low or, after PA1 triggers IC13, the timer output 2 of IC13 indicates that the predetermined time interval has passed and changes the Q output of IC14.

Figure 5:
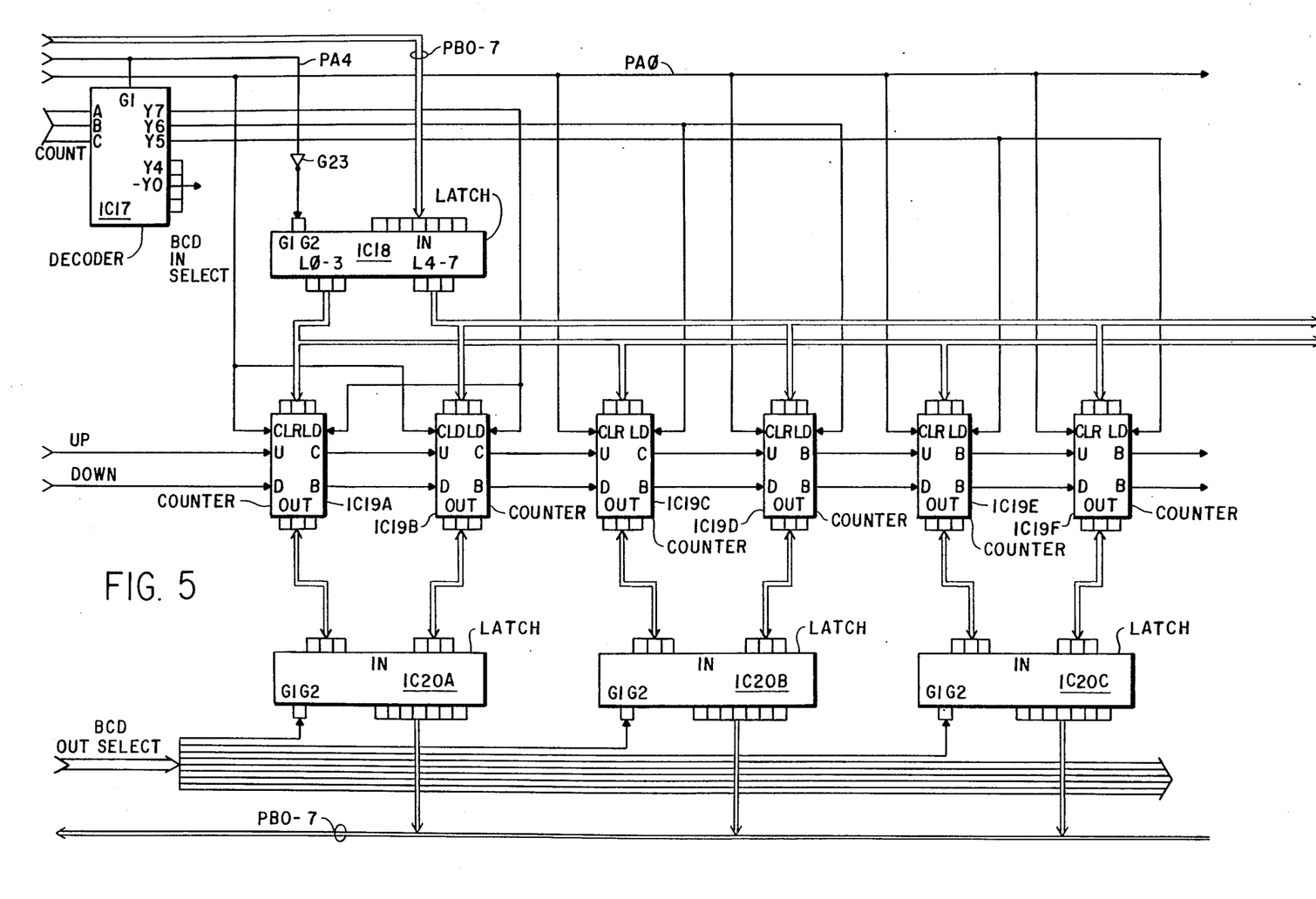
FIG. 5 is a circuit diagram of a portion of the control and computation system of FIG. 1, showing a multi-stage counter.

FIG. 5 illustrates a BCD up-down counter comprising a portion of the preferred embodiment. Counters IC19A-F are preferably BCD up-down counters which may be staged with carry and borrow lines for multiple-digit precision counting of the pulses arriving from G20 through the UP or DOWN lines. To this end, the UP line is coupled to the U input of IC19A, and the DOWN line is coupled to the D input of IC19A. The carry C output of IC19A is coupled to the U input of IC19B, and the borrow B output of IC19A is coupled to the D input of IC19B. Similar linkages are provided through each succeeding BCD counters IC19C-F.

Each BCD counter provides 4 bits of output, and the 8 output bits of each pair of BCD counters are coupled to an 8-bit latch circuit IC20, corresponding to the counter pair. Thus, in the illustrated embodiment, there are depicted six BCD counter and three corresponding latches IC20A through C. However, a large number of counters and latches can be used, and the illustrated number is not a limitation on the present invention. The 8-bit output of each latch IC20 is coupled to the corresponding eight bits of IC12 port B. The selection of one latch IC20 for among those coupled to port B may best be understood by returning to FIG. 3. PA4 and PA5 are coupled to the two inputs of exclusive OR gate G19, and the output of G19 is coupled to the clock input of binary counter IC15. PA3 is coupled through inverter G17 to the clear input of IC15, and the binary output pins of IC15 are coupled to the inputs of 3-to-8 decoder IC16. The enable input of IC16 is coupled to PA5. The eight output pins of IC16 comprise the BCD out select bus, each line of which is coupled to the latch enable and output enable pins of a corresponding IC20 in FIG. 5. Thus, when the predetermined time period passes and IC13 resets IC14 and issues an interrupt request to the processor IC1, the processor may manipulate port A of IC12 to clear IC15 and then send toggle pulses through IC15 to serially enable each IC20 through IC16. BCD counter data then passes to port B of IC12 from each IC20 when enabled, and may be retrieved from IC12 by the processor IC1.

Each IC19 has a clear CLR input, a load enable LD input and four data inputs for loading. The input bits of each pair of counters IC19 are coupled to the low and high four output bits, respectively, of latch IC18. The clear inputs of each IC19 are coupled to PA0. The pins of IC12 port B are coupled to the corresponding latch input pins of IC18. PA4 is coupled through inverter G23 to the latch input enable and output enable pins of IC18. The binary counter outputs of IC15 are coupled also to the inputs of 3-to-8 decoder IC17, and the enable input of IC17 is coupled to PA4. The outputs Y0 through Y7 of IC17 are coupled respectively to the load inputs of each pair of counter IC19. Thus, activation of the line PA4 will cause valid data to be transferred from port B of IC13 to IC18, and will allow decoder IC17 to be incremented by counter IC15 in order to select a pair of BCD counters IC19 to which data is to be transferred. In this manner, the counters may be preset to an initial value from which they may be incremented or decremented during the time period measured by IC13. The resulting counter values may then be retrieved through selection of the appropriate latches IC20 and the data thus retrieved is returned through port B of IC12 to the processor IC1.

FIG. 6 illustrates a display output and keyboard input section handled by IC10 in the preferred embodiment. The eight output pins PA0–PA7 of IC10 port A are configured for output and are coupled to the inputs D0 through D7 of 7-segment display driver IC21A. The outputs Q0 through Q7 of IC21A are coupled respectively to the inputs D0 through D7 of IC21B, and the outputs of IC21B may be similarly coupled to inputs of further display driver stages to create a serially-driven display system. The clock input of each IC21 is coupled to the ready output RDY associated with port A of IC10, so that the information arriving on driver inputs will be transferred to driver outputs. The clear inputs of each IC21 is tied through pullup resistor R17 to a five volt source. The outputs of each IC21 are also tied to the corresponding inputs of a 7-segment display device IC22 through resistors R18. Thus, in order to display a given number of digits, the processor need only provide those digits to port A of IC10 in output mode, and the first digit supplied will advance to the most remote display driver and display device in the serial system. As illustrated IC21X and IC22X are most remote, but the system may be shorter or longer as required.

Port B of IC10 is utilized on conjunction with keypad driver IC23 and hex keypad IC24. Four bits of port B are coupled to data bits D0 through D3 of IC23, and outputs Y0 through Y3 of IC23 are coupled to row inputs R0 through R3, respectively, of keypad IC24. The column outputs C0–C3 of IC24 are coupled to inputs X0–X3, respectively, of IC23. The data accepted DA output of IC23 is coupled to one input of NAND date G24, and the other input of G24 is coupled to the port B ready output of IC10. The output of G24 is coupled to the output enable input of IC23 and the port B strobe input of IC10.

The sequence of operation of the keypad begins with configuration of IC10 port B as an output port. Then data is written from the processor to port B, which forces the port B ready line to go to a high value. At this time, the DA output of IC23 is low, and therefor the G24 output is low. When the DA output goes high to indicate that data has been accepted, the G24 output goes low, which activates the port B strobe input to inform IC10 that the port B data has been received. At this time, the port B output goes low and an INT interrupt may be generated if the port is so configured. The data which has been accepted into IC23 is then written through IC23 output Y0–Y3 to select one or more rows of keyboard IC24. If one or more keys within the select row are depressed, the corresponding column bits C0–C3 will change state accordingly, causing a similar change on IC23 input pins X0–X3.

The processor meanwhile has reconfigured port B for input. Since port B has not received data, the port B ready line is high, and when X0–X3 has received data, IC23 DA goes high drive, G24 output low. Then, IC23 OE and port B strobe STB go low to signify that the data bits D0 through D3 contain valid data. Once again, IC10 may generate an interrupt so configured to inform the processor that valid data has been received in port B. The processor may then retrieve the data from IC10.

In a working version of the preferred embodiment, the following component values were used. It should be understood that such values are exemplary and in no way limit the scope of the present invention.

Resistors:
22 ohm: R5
390 ohm: R18x
1K: R1, R2
2K: R3, R6–10, R14, R16, R17, R19, R20
47K: R11, R12
82K: R4
100K: R13, R15

Capacitors:
20pF: C2
50pF: C1
100pF: C3, C4
0.1uF: C5, C6
1.0uF: C7 gates:
74SO4: G1–4, G8, G22
74LSO8: G13–15, G18
74LS14: G10, G16, G17, G20, G21, G23
74LS32: G5–7, G9, G11, G12
74LS86: G19
4011: G24 transistors:
2N2905A: Q1
BC 184: Q2–4 crystals:
8 MHz: U1, U2 integrated circuits:
Z80A: IC1
74LS74: IC2, IC14
6116: IC3, IC4
25LS2421: IC5, IC7, IC11
2732: IC6
74LS85: IC8
74LS138: IC16, IC17
74LS139: IC9
P10: IC10, IC12
CTC: IC13
74LS179: IC15
74LS244: IC18, IC20x
74LS192: IC19x
74LS273: IC21x
TIL312: IC22x
74C922: IC123

The operation of the present invention begins with the introduction of blood, treated with an agent such as citrate which serves to inhibit the Hemostasis process, into container 34. Then, upon readdition of calcium (the citrate has combined with the calcium inherent in blood), the processes of Hemostasis begin.

Electrodes 24 of transducer 20 are surrounded by blood and are coupled to an exciter and wave-shaper as described above. Substantially simultaneously with the addition of calcium to the subject blood, power is applied and processing initiated by the CPU. A typical counting procedure may begin with the CPU writing data to port A of IC12, causing PA0 to clear all counters IC19. At this time, an optional step is the repeated manipulation of PA4 and PA5 to select pairs of BCD counters IC19, coupled with the transmission of data from the CPU through IC12 port B and latch IC18 to set each pair of BCD counters IC19 to specific values. Timing data is then written by the CPU to the timer registers of IC12, following which data is written to IC12 to activate PA1 and select an increment or decrement counting mode by the status of PA2. During the time period determined by the data written to the timers of IC13, the output pulses of exciter and waveshaper 14 are counted by the BCD counters IC19. When the predetermined time period has expired, the Q output of IC14 halts the counting of pulses, and IC13 may issue an interrupt to the CPU.

The CPU then reconfigures IC12 port B to receive data, and manipulates PA5 to sequentially select an output latch IC20 coupled to IC12 port B. Thus, the BCD counter data from each pair of counters IC19 will be transferred to port B and may be read by the central processing unit.

The keypad IC24 may be utilized to select among alternative program segments corresponding to different algorithms necessary for determinations of specific apsects the Hemostatic processes outlined previously.

In the foregoing description, the invention has been described with reference to a particular preferred embodiment, although it is to be understood that the specific details shown are merely illustrative and that the invention may be carried out in other ways without departing from the true spirit and scope of the following claims.

What is claimed is:

1. An apparatus for measuring blood viscosity changes during coagulation comprising, in combination: a housing of known volume adapted to receive blood therein; an oscillating member and post means contained in said housing at a distance from one another such that said blood can fill the distance by capillary action and adapted to be immersed in blood received in said housing; said oscillating member being composed of crystal which is capable of producing vibrations having frequencies from 100 hertz to 1 megahertz, computation means adapted to measure oscillations of said oscillating member as a functional of a known time period and calculate viscosity of blood, said computation means comprising a digital computer and algorithms stored on magnetic media adapted to be executed by said digital computer, said oscillating member connected to said computation means; and a display means coupled to said computing means and adapted to display said calculated viscosity of blood.

2. An apparatus as claimed in claim 1 wherein said oscillating member is a crystal and the opposing sides of said oscillating crystal are coated with a conducting substance, with said computation means being adapted to measure the capacitance of said conducting substance.

3. An apparatus as claimed in claim 1 wherein said housing contains an input channel whereby blood enters said container by capillary action.

4. An apparatus as claimed in claim 1 wherein said display means generates a digital output.

5. An apparatus as claimed in claim 1 wherein said display means generates graphic output.

6. An apparatus for measuring changes in blood viscosity comprising, in combination: switching means, computation means, a plurality of housing of known volume, each adapted to receive blood therein; an oscillating member contained in each said housing and adapted to be immersed in blood received by each said housing; each of said oscillating members being disposed such that the space between said member and a wall of said housing can be filled by capillary action; each of said members being coupled to said switching means; crystal excitation and wave-shaping circuit means connected to each said oscillating member, said crystal excitation and wave-shaping circuit being utilized to produce a master clock signal, said switching means connected to said computation means whereby said computation means may be selectively connected to any of said oscillating members via, said switching means; and a display means coupled to said computing means and adapted to display viscosity of blood.

7. A method for the determination of changes in various parameters of blood during the process of hemostasis in human blood, comprising the steps of:
   a. immersing an oscillating member maintained in a housing of known volume at a distance from a wall of said housing such that the space can be filled by capillary action;
   b. sensing the vibration of said oscillating member a predetermined number of times over an known time period X beginning simultaneously with said immersion of oscillating member into said blood;
   c. computing the frequency of vibration of said oscillating member as a function of known time period X at a time post operatively of said immersion of oscillating member in said blood;
   d. determining the viscosity of said blood in correlation with the process of blood hemostasis by comparison of said frequencies determined in steps b and c with a central processing unit; and
   e. displaying said viscosity of said blood relative to its correlative hemostasis parameter.

8. A method for the determination of various parameters of the process of hemostasis in human blood as set forth in claim 7 wherein said method contemplates the utilization of a plurality of oscillating members in a plurality of housings of known volume which utilize the same computation and display means.

9. A method for the determination of changes in various parameters of blood during the process of hemostasis in human blood, comprising the steps of:
   a. introducing blood by capillary action into an interval void located in a housing of known volume, said housing containing a oscillating member and a solid member which defines therebetween the interval void;
   b. selecting a desired program segment corresponding to different algorithms necessary for determinations of specific predetermined aspects of the process of hemostasis with a keyboard;
   c. sensing the solidification of said human blood by computing vibration of said oscillating member over known time period X beginning simultaneously with the introduction of said blood to said oscillating member wherein the vibrations of said oscillating member degenerate in conjunction with the solidification of said blood;
   d. computing the degradation of said oscillating member as solidification occurs in said blood; and
   e. displaying said viscosity of blood by generating digital output containing the periods of vibration of said oscillating member, and the degradation of vibrations thereof to represent to a specific aspect of hemostasis.

* * * * *